United States Patent [19]

Bourgogne et al.

[11] Patent Number: 4,496,528
[45] Date of Patent: Jan. 29, 1985

[54] PROCESS FOR THE PREPARATION OF ZEOLITE ZK 5

[75] Inventors: Michel Bourgogne, Reidisheim; Jean-Louis Guth, Brunstatt; Georges Szabo, Montivilliers; Raymond Wey, Mulhouse, all of France

[73] Assignee: Compagnie Francaise de Raffinage, Paris, France

[21] Appl. No.: 480,037

[22] Filed: Mar. 29, 1983

[30] Foreign Application Priority Data

Apr. 1, 1982 [FR] France ............................. 82 05665

[51] Int. Cl.$^3$ .............................................. C01B 33/28
[52] U.S. Cl. .................................... 423/328; 423/331; 423/332; 502/60
[58] Field of Search ............... 423/328, 329, 331, 332; 502/77, 60

[56] References Cited

U.S. PATENT DOCUMENTS

| | | | |
|---|---|---|---|
| 2,413,134 | 12/1946 | Barrer | 423/131 |
| 3,247,195 | 4/1966 | Kerr | 423/328 |
| 3,691,099 | 9/1972 | Young | 423/328 |
| 3,720,753 | 3/1973 | Robson | 423/329 |

OTHER PUBLICATIONS

R. M. Barrer et al., "Hydrothermal Chemistry of Silicates, Part XV, Synthesis and Nature of Some Salt Bearing Aluminosilicates", J. of the Chemical Soc., Section A, Inorg., Physical and Theoretical Chemistry, pp. 2735-2745, (1970).
Richard M. Barrer et al., "Hydrothermal Chemistry of Silicates, Part 21, Zeolites from Reaction of Li and Cs Ions with TMA Aluminosilicate Solutions", J. of the Chemical Soc. Dalton Transactions, pp. 1020-1026, (1977).
George T. Kerr, "Chemistry of Crystalline Aluminosilicates, III, The Synthesis and Properties of Zeolite ZK -5", *Inorganic Chemistry* vol. 5, No. 9, Sep. 1966, pp. 1539-1541.
J. C. Bailar, Ed., *Comprehensive Inorganic Chemistry*, vol. 1, 1973, Pergammon Press, pp. 614-615.

Primary Examiner—Edward J. Meros
Assistant Examiner—Jackson Leeds
Attorney, Agent, or Firm—Curtis, Morris & Safford

[57] ABSTRACT

The invention relates to the preparation of the zeolite ZK-5 from a starting zeolite selected from the group consisting of the zeolites P (Cl), P' (Cl), Q (Br) and Q' (Br).

In accordance with the invention, the barium ions contained in the starting zeolite are extracted therefrom by means of a barium-binding agent selected from the group consisting of precipitating agents which form with the barium ions a compound that precipitates, and of complexing agents which form with the barium ions a barium complex.

The zeolite ZK-5 obtained may be used in the separation or cracking of hydrocarbons.

38 Claims, No Drawings

PROCESS FOR THE PREPARATION OF ZEOLITE ZK 5

The present invention relates to a process for the preparation of the zeolite ZK 5. The invention further relates to applications of said zeolite, particularly in the separation of compounds such as hydrocarbons and as a hydrocarbon cracking catalyst.

The zeolites form a family of alkali-metal or alkaline-earth metal aluminosilicates which comprises several dozen compounds existing in the natural state.

The structure of the zeolites may be defined as a three-dimensional framework of tetrahedra of the formula $SiO_4$ and $AlO_4$ linked by oxygen bridges. This framework, whose geometry varies from one zeolite to the next, forms an array of cavities which are interconnected by openings of varying shapes and dimensions, the characteristics of the array being representative of a given zeolite. The cavities are occupied by ions or water molecules having pronounced mobility.

Zeolites can be distinguished from one another by their chemical composition, and more particularly, in a precise manner, by their x-ray diffraction spectrum. The latter makes it possible to determine the spacings d between the lattice planes of the crystals, expressed in angstroms (Å), and the relative intensities of the lines of the diffraction pattern.

Minor changes in the interplanar spacings and in the intensities which may be observed in some patterns are due to variations in chemical composition, such as the replacement of certain cations by others, or to variations in the $SiO_2/Al_2O_3$ ratio. They do not, however, indicate a significant structural change in the zeolite.

Its pore size permits a given zeolite to adsorb or reject given molecules, depending on their size.

Zeolites have therefore been used to separate different compounds, as, for example, in the drying or purification of gases. They are also used as catalysts or carriers of catalysts for the conversion of compounds, for example, in hydrocarbon cracking, alkylation or isomerization reactions.

The interesting properties of the zeolites have led to a search for manufacturing processes for synthetic zeolites. Many zeolites have been synthesized and form the subject matter of numerous patents.

Synthetic zeolites are commonly designated by a symbol, as, for example, the zeolites A, X, Y, W, ZSM-11, ZSM-12, etc.

One particular zeolite, the ZK 5, has been prepared by a process described in the work by D. W. Breck, "Zeolite Molecular Sieves", on pages 309 to 310.

This method consists in adding to an aluminosilicate gel a nitrogenated dibasic cation of the formula

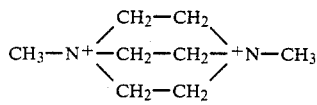

This cation is introduced in the form of a silicate of 1,4-dimethyl-1-1,4-diazoniacyclo(2,2,2)octane.

The ratios of the components of the reaction mixture are as follows:

$SiO_2/Al_2O_3$:4 to 11
$Na_2O/Al_2O_3 + C_8H_{18}N_2O/Al_2O_3$:6 to 19
$Na_2O/Al_2O_3$:1.5 to 2.3
$H_2O/Al_2O_3$:200 to 700

The alumina is added in the form of a solution of sodium aluminate, which is then mixed with the quaternary ammonium silicate solution to form an amorphous gel. The ZK 5 is obtained by heating the reaction mixture to 100° C. for 9 days. The zeolite obtained has the following chemical composition:

0.3–0.7$Na_2O$/0.3–0.7$RO$/$Al_2O_3$/4.0–6.0$SiO_2$/6–10-$H_2O$, wherein $R = C_{18}H_{18}N_2{}^{2+}$.

This method has the drawback that it requires the use of an expensive product, namely, the silicate of 1,4-dimethyl-1-1,4-diazoniacyclo(2,2,2)octane.

Another method consists in preparing one of the intermediate phases, called P (Cl), P' (Cl), Q (Br) or Q' (Br). These intermediate phases are obtained by reacting a barium halide with a gel of barium or potassium aluminosilicate (see U.S. Pat. No. 2,413,134) or with certain zeolites such as analcite (see also U.S. Pat. No. 2,413,134), zeolite Y, zeolite X or chabazite (see the article by R. M. Barrer and C. Marcilly, "Synthesis and Nature of some Salt-Bearing Aluminosilicates", which appeared in The Journal of the Chemical Society, section A, Inorganic, Physical and Theoretical Chemistry, pp. 2735-2745 [1970]).

That patent and that article give as operating conditions temperatures of at least 100° C. and as high as 400° C. and reaction periods of several days.

If the barium halide is barium chloride, zeolite P (Cl) or P' (Cl) is obtained. If the barium halide is barium bromide, zeolite Q (Br) or Q' (Br) is obtained.

The zeolites P (Cl) or Q (Br) are obtained from analcite or from zeolite Y, and the zeolites P' (Cl) or Q' (Br) from zeolite X.

These zeolites contain barium as exchange cation and the barium halide as an occluded salt.

The halide is then extracted from the zeolite by washing either with water, as described in U.S. Pat. No. 2,413,134, or with solutions of a nitrate (for example, sodium nitrate), as described in said article by Barrer and Marcilly. A zeolite is thus obtained which has the structure of the zeolite ZK 5.

However, these methods have the drawback of being time-consuming and because of the severe washing conditions often result in a recrystallization of the zeolite into other phases. (In this connection, refer to Table 6 on page 2739 of the article by Barrer and Marcilly.)

Applicants have developed a simpler process for the preparation of zeolite ZK 5.

The object of the invention thus is a process for the preparation of the zeolite ZK 5 from a starting zeolite selected from the group consisting of the zeolites P (Cl), P' (Cl), Q (Br) and Q' (Br), the starting zeolite being prepared conventionally, said process being characterized in that the barium ions contained in the starting zeolite are extracted therefrom by means of a barium-binding agent selected from the group consisting of precipitating agents which form with the barium ions a compound that precipitates, and of complexing agents which form with the barium ions a barium complex.

In the mode of carrying out the process of the invention which uses a precipitating agent, the latter is selected from among soluble compounds capable of forming with barium an insoluble compound that is readily separable from the zeolite ZK 5 without altering the structure of the latter. Suitable agents of this type include the rhodizonates, the oxalates and the carbonates of alkali metals or ammonium. When an alkali-metal or ammonium carbonate is used, a precipitate of barium carbonate is formed which is readily removed from the zeolite by dissolution at a pH between 1 and 5.5 with solutions of the type of acetic buffer mixtures, dilute hydrochloric acid, etc.

If a complexing agent is used, the latter is selected from among soluble compounds, such as the salts of ethylenediamine tetraacetic acid (EDTA) or diethylenetriamine pentaacetic acid (DTPA), which are capable of forming soluble complexes with the barium ions. In this case, the zeolite ZK 5 is obtained by simple filtration of the solution containing the complexes formed with the barium.

In the process of the invention, the starting zeolite may therefore be a P (Cl) or P' (Cl) zeolite in particular.

The x-ray diffraction patterns of the zeolites P (Cl) and P' (Cl) are given in Table 1 which follows, where d denotes the interplanar spacing, expressed in Å (angstroms), and $I/I_o$ the relative intensity of the lines of the pattern.

TABLE 1

| P (Cl) | | P' (Cl) | |
|---|---|---|---|
| d (Å) | $I/I_o$ | d (Å) | $I/I_o$ |
| 13.20 | 100 | — | — |
| 9.36 | 15 | — | — |
| — | — | 5.93 | 19 |
| 4.99 | 22 | 5.01 | 60 |
| 4.64 | 11 | — | — |
| 4.39 | 77 | 4.43 | 80 |
| 4.17 | 36 | 4.20 | 57 |
| 3.96 | 9 | — | — |
| 3.80 | 47 | 3.84 | 40 |
| 3.66 | 20 | — | — |
| 3.29 | 15 | 3.32 | 27 |
| 3.19 | 63 | 3.22 | 38 |
| 3.11 | 14 | 3.13 | 30 |
| 3.03 | 94 | 3.05 | 100 |
| 2.95 | 6 | — | — |
| 2.87 | 18 | 2.90 | 22 |
| 2.81 | 83 | 2.84 | 57 |
| 2.74 | 6 | 2.77 | 26 |
| 2.69 | 6 | 2.71 | 17 |
| 2.63 | 26 | 2.66 | 17 |
| 2.58 | 13 | 2.60 | 26 |
| 2.53 | 35 | 2.56 | 65 |

The operating conditions which may be used in the process of the invention to extract $BaCl_2$ from zeolite P (Cl) or zeolite P' (Cl) are given in Table 2 which follows for different extraction agents.

When an alkali-metal or ammonium carbonate is used to extract the barium ions, the barium carbonate precipitate is dissolved at a pH between 1 and 5.5, without alteration of the structure of the zeolite, with solutions such as the acetic buffers $CH_3COOH/CH_3COONa$ and $CH_3COOH/CH_3COONH_4$, dilute hydrochloric acid, etc.

The operating conditions for the dissolution of the barium carbonate at a pH between 1 and 5.5 are given in Table 3 which follows for the cases indicated above.

TABLE 3

| Agents dissolving barium carbonate | Parameters | | | | | |
|---|---|---|---|---|---|---|
| | A | B | | C | | D |
| | BR | BR | PR | BR | PR | BR |
| Acetic buffers | 0.5 M–2 M | 5–30 | 8–25 | 10–100 | 15–60 | 5–20 |
| Hydrochloric acid | M/100–M/4 | 5–30 | 8–25 | 10–25 | | 5–20 |

A = Concentration of solvent (moles/liter)
B = Liquid/solids ratio by weight
C = Temperature (°C.)
D = Treating time (minutes)
BR = Broad range
PR = Preferred range The general formula of the zeolite ZK 5 prepared by the process of the invention is $$0.5–0.9 M_2O/0.2–0.5 BaO/Al_2O_3/2.5–7 SiO_2/0–0.3 BaCl_2/0–7 H_2O,$$

where M is an alkali-metal cation.

Its x-ray diffraction pattern is given in Table 4 which follows.

TABLE 4

| d (Å) | $I/I_o$ |
|---|---|
| 13.26 | 50 |
| 9.34 | 100 |
| 7.65 | 12 |
| 6.60 | 15 |
| 5.92 | 22 |
| 5.40 | 34 |
| 5.01 | 15 |
| 4.67 | 9 |
| 4.42 | 56 |
| 4.19 | 50 |
| 3.99 | 26 |
| 3.83 | 40 |
| 3.67 | 15 |
| 3.42 | 19 |
| 3.30 | 9 |
| 3.21 | 44 |
| 3.12 | 11 |
| 3.05 | 74 |
| 2.96 | 23 |
| 2.89 | 9 |

TABLE 2

| | PARAMETERS | | | | | | | | | |
|---|---|---|---|---|---|---|---|---|---|---|
| | A | | B | | C | | D | | E | |
| Extractant | BR | PR | BR | PR | BR | PR | BR | PR | BR | PR |
| Alkali-metal or ammonium carbonates | M/10–2M | M/5–1.5M | M/10–2M | M/4–M | 2–25 | 5–20 | 20–280 | 80–200 | 0.5–192 | 1–120 |
| EDTA salts | M/10–2M | M/5–M | M/10–2M | M/5–1.5M | 2–25 | 5–20 | 40–180 | 60–150 | 6–192 | 12–96 |
| DTPA salts | M/10–2M | M/5–M | M/2–2M | M–1.5M | 2–25 | 5–20 | 20–125 | 40–110 | 6–144 | 12–72 |

A = Concentration of barium-binding agent (moles/liter)
B = Concentration (moles/liter) of a base, such as sodium, which may be used together with the extractant
C = Liquid/solids ratio by weight
D = Temperature (°C.)
E = Treating time (hours)
BR = Broad range
PR = Preferred range TABLE 4-continued

| d (Å) | I/I$_o$ |
| --- | --- |
| 2.83 | 53 |
| 2.77 | 19 |
| 2.71 | 11 |
| 2.65 | 22 |
| 2.60 | 7 |
| 2.55 | 22 |

The invention makes it possible to obtain the zeolite ZK 5 in powder form or conditioned from zeolites P (Cl), P' (Cl), Q (Br) or Q' (Br) in powder form or already conditioned, that is to say, agglomerated (pellets, granules, extrusions, etc.) without binder. The shaping of the zeolites is done by conventional methods; the pressure used should not exceed 10 tons/cm$^2$. The agglomeration of the powder may be carried out in the presence of water, in which case the weight of the water should not exceed 50 percent of the weight of the zeolite involved.

The zeolite ZK 5 prepared by the process of the invention is suited for use especially in the separation of straight-chain saturated aliphatic hydrocarbons, branchedchain saturated aliphatic hydrocarbons, cyclic saturated hydrocarbons or aromatic hydrocarbons.

It is further suited for use as a hydrocarbon cracking catalyst.

The examples which follow will serve to illustrate the invention without limiting it.

Example 1 relates to the preparation of zeolites P (Cl) or P' (Cl).

Example 2 relates to the preparation of zeolites ZK 5 from zeolites P (Cl) or P' (Cl) prepared according to Example 1.

Example 3 relates to adsorption tests for different hydrocarbons run with zeolites ZK 5 prepared according to Example 2.

Example 4 relates to hydrocarbon cracking tests with a zeolite prepared according to Example 2.

EXAMPLE 1

This example relates to the preparation of zeolites P (Cl) or P' (Cl).

Preparatory Procedure 1

In a 500-ml polytetrafluoroethylene flask there were reacted:
20 g of the sodium form of faujasite Y in powder form with an SiO$_2$/Al$_2$O$_3$ ratio of 4.2
3.5 g of amorphous silica in powder form containing 16 weight percent water
240 g of barium chloride, BaCl$_2$.2H$_2$O 240 ml water The overall SiO$_2$/Al$_2$O$_3$ ratio of the reaction mixture was 5.5.

The polytetrafluoroethylene flask was placed in an autoclave which was heated to 250° C. for 100 hours. The reaction mixture was then filtered and the solid obtained was dried at 60° C.

28.7 g of a product was thus obtained which was identified as a zeolite P (Cl) by its x-ray diffraction spectrum. Analysis of the product showed that it had the following composition:

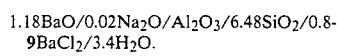

1.18BaO/0.02Na$_2$O/Al$_2$O$_3$/6.48SiO$_2$/0.8-9BaCl$_2$/3.4H$_2$O.

Preparatory Procedure 2

In a 1-liter polytetrafluoroethylene flask there were reacted:
50 g of the sodium form of faujasite Y in the form of extrusions with an SiO$_2$/Al$_2$O$_3$ ratio of 4.98
600 g of barium chloride, BaCl$_2$.2H$_2$O 600 ml water The polytetrafluoroethylene flask was placed in an autoclave which was heated to 250° C. for 120 hours. The reaction mixture was then filtered and the solid obtained was dried at 60° C.

71 g of a product was thus obtained which was identified as a zeolite P (Cl) by its x-ray diffraction spectrum. It had the following formula:

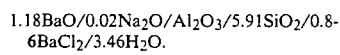

1.18BaO/0.02Na$_2$O/Al$_2$O$_3$/5.91SiO$_2$/0.8-6BaCl$_2$/3.46H$_2$O.

Preparatory Procedure 3

The preceding experiment was repeated, except that this time a sodium-type faujasite X was used in the form of extrusions with an SiO$_2$/Al$_2$O$_3$ ratio of 2.5.

After conversion, filtration and drying at 60° C., 72 g of zeolite P' (Cl), identified by its x-ray diffraction spectrum, was obtained which had the following formula:

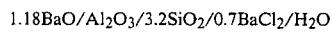

1.18BaO/Al$_2$O$_3$/3.2SiO$_2$/0.7BaCl$_2$/H$_2$O

The high SiO$_2$/Al$_2$O$_3$ ratio of the zeolites obtained by the three preparatory procedures of this Example is due both to a partial extraction of the aluminum during the conversion and to the presence of a little residual amorphous silica in the final product upon conversion in the presence of silica.

EXAMPLE 2

This example relates to the preparation of zeolites ZK 5 from zeolites P (Cl) or P' (Cl) prepared according to Example 1.

Preparatory Procedure 1

1 g of zeolite P (Cl) prepared by procedure 1 of Example 1 was treated with an aqueous sodium carbonate solution containing 1 mole sodium carbonate per liter. The liquid/solid ratio by weight was 10 in this treatment. The treatment was carried out at 110° C. for 72 hours. The barium carbonate which formed precipitated. Filtration yielded a solid which was dried at 60° C.

The barium carbonate was separated from the zeolite by dissolution with a solution containing one mole of sodium acetate per mole of acetic acid per liter. Dissolution was carried out at about 20° C. by agitating the mixture for about 10 minutes, the liquid/solid weight ratio being 20.

Filtration yielded 690 mg of a solid, which was dried at 60° C. The x-ray diffraction spectrum of that solid corresponded to that of a zeolite ZK 5 with the formula:

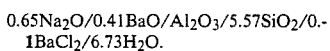

0.65Na$_2$O/0.41BaO/Al$_2$O$_3$/5.57SiO$_2$/0.1BaCl$_2$/6.73H$_2$O.

Preparatory Procedure 2

10 g of zeolite P (Cl), prepared by procedure 1 of Example 1, was treated with an aqueous sodium carbonate solution containing one-half mole sodium carbonate per liter. The liquid/solid weight ratio during this treatment was 8. The treatment was carried out at 150° C. for 60 hours. After filtration and drying of the solid obtained, the barium carbonate was dissolved by means of a solution containing one mole of sodium acetate per mole of acetic acid per liter. Dissolution was carried out under the same conditions as in procedure 1, the liquid/solid weight ratio being 10.

6.3 g of zeolite ZK 5, identified by its x-ray spectrum, was obtained. Its formula was:

0.54BaO/0.53Na$_2$O/Al$_2$O$_3$/5.66SiO$_2$/0.04BaCl$_2$/6.78H$_2$O.

Preparatory Procedure 3

5 g of zeolite P (Cl), prepared by procedure 1 of Example 1, was treated with an aqueous sodium carbonate solution containing one-half mole sodium carbonate per liter. The liquid/solid weight ratio during this treatment was 15. The treatment was carried out at 250° C. for 2 hours. After filtration and drying of the solid obtained at 60° C., the barium carbonate was dissolved by means of a tenth-molar hydrochloric acid solution at about 20° C. by agitation of the mixture for about 10 minutes, the liquid/solid weight ratio being 15.

3.4 g of zeolite ZK 5, identified by its x-ray diffraction spectrum, was obtained. Its formula was:

0.59BaO/0.49Na$_2$O/Al$_2$O$_3$/5.79SiO$_2$/0.1BaCl$_2$/6.53H$_2$O.

Preparatory Procedure 4

50 g of a zeolite P (Cl), prepared by an operating procedure analogous to preparatory procedure 1 of Example 1, was treated with an aqueous solution containing one-half mole ammonium carbonate and one-half mole sodium per liter, the liquid/solid weight ratio being 10. The treatment was carried out at 100° C. for 72 hours. After filtration and drying of the solid obtained, the barium carbonate was dissolved by means of a solution containing one mole ammonium acetate per mole acetic acid per liter. Dissolution was carried out at about 20° C. by agitation of the mixture for about 10 min., the liquid/solid weight ratio being 20. 32.5 g of zeolite ZK 5, identified by its x-ray spectrum, was obtained. Its formula was:

0.59Na$_2$O/0.48BaO/Al$_2$O$_3$/5.17SiO$_2$/0.06BaCl$_2$/5.62 H$_2$O.

Preparatory Procedure 5

50 g of zeolite P (Cl), prepared by procedure 2 of Example 1, was treated with an aqueous solution of the disodium salt of ethylenediamine tetraacetic acid containing one-fourth mole of said salt and one-half mole sodium per liter.

The liquid/solid weight ratio was 10. The treatment was carried out at 110° C. for 72 hours. The barium was complexed, in the presence of the ethylenediamine tetraacetic anion [N$_2$(CH$_2$)(CO$_2$CH$_2$)$_4$]$^{2-}$-H$_2$ and in a basic medium, in accordance with the reaction Ba$^{2+}$+[N$_2$(CH$_2$)$_2$(CO$_2$CH$_2$)$_4$]$^{2-}$-H$_2$→Ba[N$_2$(CH$_2$)$_2$(CO$_2$CH$_2$)$_4$]$^{2-}$+2H$^+$.

After filtration and drying at 60° C., 35.6 g of a solid having the x-ray spectrum of a zeolite ZK 5 was obtained. Its formula was:

0.79Na$_2$O/0.22BaO/Al$_2$O$_3$/5.67SiO$_2$/0.07BaCl$_2$/5.70H$_2$O.

Preparatory Procedure 6

20 g of zeolite P (Cl), prepared by procedure 2 of Example 1, was treated with an aqueous solution of the disodium salt of EDTA containing one-fourth mole of said salt and one-half mole of sodium per liter.

The liquid/solid weight ratio was 8. The treatment was carried out at 80° C. for 60 hours. After filtration and drying at 60° C., 15.6 g of zeolite ZK 5, identified by its x-ray spectrum, was obtained. Its formula was:

0.67Na$_2$O/0.43BaO/Al$_2$O$_3$/5.62SiO$_2$/5.62H$_2$O.

Preparatory Procedure 7

3 g of zeolite P (Cl), prepared by procedure 2 of Example 1, was treated with a solution of the disodium salt of EDTA containing one-fourth mole of said salt and one-half mole of sodium. The liquid/solid weight ratio was 10. The treatment was carried out at 125° C. for 24 hours. After filtration and drying at 60° C., 2.1 g of zeolite ZK 5, identified by its x-ray spectrum, was obtained. Its formula was:

0.74Na$_2$O/0.37BaO/Al$_2$O$_3$/SiO$_2$/5.61H$_2$O.

Preparatory Procedure 8

100 g of a zeolite P (Cl), prepared by an operating procedure analogous to preparatory procedure 1 of Example 1, was treated with an aqueous solution of the disodium salt of EDTA containing one-half mole of said salt and one mole of sodium per liter. The liquid/solid weight ratio was 10. The treatment was carried out at 100° C. for 72 hours.

After filtration and drying at 60° C., 60 g of zeolite ZK 5, identified by its x-ray spectrum, was obtained. Its formula was:

0.94Na$_2$O/0.17BaO/Al$_2$O$_3$/5.15SiO$_2$/0.2BaCl$_2$/5.85H$_2$O.

Preparatory Procedure 9

20 g of a zeolite P (Cl), prepared by an operating procedure analogous to preparatory procedure 1 of Example 1, was treated with a solution composed of a solvent formed by a mixture of 50 volume percent water and 50 volume percent ethyl alcohol and containing one-half mole of the disodium salt of EDTA and one mole of sodium per liter. The liquid/solid weight ratio during this treatment was 15. The treatment was carried out at 80° C. for 72 hours.

After filtration and drying at 60° C., 10 g of zeolite ZK 5, identified by its x-ray spectrum, was obtained. Its formula was:

1.01Na$_2$O/0.18BaO/Al$_2$O$_3$/4.92SiO$_2$/0.3BaCl$_2$/5.64H$_2$O.

Preparatory Procedure 10

20 g of a zeolite P (Cl), prepared by procedure 2 of Example 1, was treated with a solution of diethylenetriamine pentaacetic acid (DTPA) containing one-fourth mole of said acid and 1.25 moles of sodium per liter. The liquid/solid weight ratio was 10. The treatment was carried out at 60° C. for 90 hours. After filtration and drying at 60° C., 12.4 g of zeolite ZK 5, identified by its x-ray spectrum, was obtained. Its formula was:

0.81Na$_2$O/0.27BaO/Al$_2$O$_3$/5.62SiO$_2$/0.14BaCl$_2$/5.65H$_2$O.

Preparatory Procedure 11

50 g of zeolite P (Cl), prepared by procedure 2 of Example 1, was treated with a solution of DTPA containing one-fourth mole of said acid and 1.25 moles of sodium per liter. The liquid/solid weight ratio was 10. The treatment was carried out at 85° C. for 72 hours. After filtration and drying at 60° C., 35 g of zeolite ZK 5, identified by its x-ray spectrum, was obtained. Its formula was:

$0.83Na_2O/0.25BaO/Al_2O_3/5.69SiO_2/0.09BaCl_2/5.52H_2O$.

Preparatory Procedure 12

100 g of zeolite P (Cl), prepared by procedure 2 of Example 1, was treated with a solution of DTPA containing one-fourth mole of said acid and 1.25 moles of sodium per liter. The liquid/solid weight ratio was 10. The treatment was carried out at 100° C. for 48 hours. After filtration and drying at 60° C., 71 g of zeolite ZK 5, identified by its x-ray spectrum, was obtained. Its formula was:

$0.82Na_2O/0.26BaO/Al_2O_3/5.55SiO_2/0.04BaI_2/5.63H_2O$.

Preparatory Procedure 13

50 g of zeolite P' (Cl), prepared by procedure 3 of Example 1, was treated with an aqueous solution of the disodium salt of ethylenediamine tetraacetic acid containing one-fourth mole of said salt and one-half mole of sodium. The liquid/solid weight ratio was 10. The treatment was carried out at 110° C. for 72 hours. After filtration and drying, 30 g of zeolite ZK 5, identified by its x-ray spectrum, was obtained. Its formula was:

$0.80Na_2O/0.21BaO/Al_2O_3/3SiO_2/0.05BaCl_2/7.3H_2O$.

EXAMPLE 3

This example relates to adsorption tests for different hydrocarbons run with the zeolites ZK 5 prepared according to Example 2.

Tests A

The adsorption measurements were made by gravimetric methods using a MacBain type of balance with silicaglass springs.

After degasification and dehydration by heating to 350° C. under a vacuum of $10^{-2}$ mm Hg for 2 hours, the samples of zeolite ZK 5 were contacted with a gaseous hydrocarbon, normal hexane or cyclohexane. The hydrocarbon was at the vapor pressure of the hydrocarbon involved at 13° C., the hydrocarbon vapors coming from a source maintained at 13° C.

The measurement was made when the temperature of the zeolite, initially 350° C., had dropped to 20° C.

The results of these tests are presented in Table 5 which follows.

TABLE 5

| Sample of zeolite ZK 5 prepared by procedure | Grams of n-hexane adsorbed per 100 g of anhydrous sample | Grams of cyclohexane adsorbed per 100 g of anhydrous sample |
| --- | --- | --- |
| 1 | 11.85 | Not measured |
| 2 | 12.98 | 1.35 |
| 3 | 10.20 | Not measured |
| 4 | 11.95 | — |
| 5 | 10.87 | — |
| 6 | 8.43 | — |
| 7 | 9.96 | — |
| 8 | 13.94 | 0.75 |
| 10 | 9.86 | Not measured |
| 11 | 11.00 | — |
| 12 | 10.86 | 1.25 |

It is apparent from this table that zeolite ZK 5 adsorbs normal hexane much better than cyclohexane and can thus be used to separate these two hydrocarbons.

Tests B

These adsorption tests were run with a zeolite ZK 5 which had been prepared by an operating procedure analogous to preparatory procedure 4 of Example 2 from a zeolite P (Cl) prepared by an operating procedure analogous to preparatory procedure 1 of Example 1.

The sample was degasified and dehydrated by being heated to 300° C. under a vacuum of $10^{-3}$ mm Hg for 18 hours. After its temperature had dropped to 20° C., the sample was contacted for 4 hours with different hydrocarbons in the gas phase.

The hydrocarbon was at the vapor pressure of the hydrocarbon involved at 0° C., the hydrocarbon vapors coming from a source maintained at 0° C.

The sample was weighed before and after each adsorption to determined the weight percent of hydrocarbon adsorbed, which were as follows:

Normal hexane: 7.83%
3-methyl pentane: 0%
Benzene: 0.67%
Cyclohexane: 0.10%

These tests show that the zeolite ZK 5 can be used to separate different hydrocarbons having the same number of carbon atoms.

EXAMPLE 4

This example relates to hydrocarbon cracking tests run with a zeolite ZK 5 identical to that used in the tests B of Example 3.

Before the actual cracking tests, the zeolite ZK 5, which was present in the sodium form, was subjected to a treatment to convert it to the acid form, that is to say, to replace the sodium ions with hydrogen ions.

The zeolite was treated three times with an ammonium chloride solution at a temperate of 80° C. for 2 hours. After each treatment it was dewatered and then calcined at 550° C.

The H-type zeolite ZK 5 so obtained was used to crack at different temperatures a charge formed by a mixture composed of 50% normal hexane and 50% 3-methyl pentane. The effluent gases from the cracking reactor were analyzed by chromatography to determine the degree of conversion of normal hexane and 3-methyl pentane.

The results obtained are presented in Table 6 which follows.

TABLE 6

| Temperature | Conversion (%) of | |
|---|---|---|
| (°C.) | Normal hexane | 3-methyl pentane |
| 290 | 17.01 | 0 |
| 320 | 19.86 | 0 |
| 360 | 20.75 | 0 |
| 410 | 28.83 | 0 |
| 450 | 30.45 | 0 |

The zeolite ZK 5 prepared by the process of the invention thus is a good, selective hydrocarbon cracking catalyst.

We claim:

1. A process for the preparation of zeolite ZK 5 from a starting zeolite selected from the group consisting of zeolites P (Cl), P' (Cl), Q (Br) and Q' (Br), comprising extracting barium ions contained in the starting zeolite by means of a barium-binding agent selected from the group consisting of precipitating agents which form with the barium ions a compound that precipitates, and of complexing agents which form with the barium ions a barium complex.

2. A process according to claim 1, wherein the precipitating agent is selected from the group consisting of rhodizonates, oxalates, and carbonates of alkali metals and ammonium carbonate.

3. A process according to claim 2, wherein the precipitating agent is a carbonate selected from the group consisting of ammonium carbonate and carbonates of an alkali metal, and the barium carbonate formed is dissolved at a pH between 1 and 5.5 by means of a solution selected from the group consisting of acetic buffer mixtures and dilute hydrochloric acid.

4. A process according to claim 1, wherein the complexing agent is selected from the group consisting of soluble compound capable of forming with barium ions soluble complexes which are separable from the zeolite ZK 5 by filtration.

5. A process according to claim 4, wherein the complexing agent is selected from the group consisting of the salts of ethylenediamine tetraacetic acid and diethylenetriamine pentaacetic acid.

6. A process according to claim 3, wherein upon extraction the liquid/solid weight ratio is from 2:1 to 25:1.

7. A process according to claim 6, wherein the ratio is from 5:1 to 20:1.

8. A process according to claim 3, wherein upon extraction the concentration of the precipitating agent, in moles per liter, is from M/10 to 2 M.

9. A process according to claim 8, wherein the concentration is from M/5 to 1.5 M.

10. A process according to claim 3, wherein a base is used together with the extraction agent, and the concentration of said base, in moles per liter, is from M/10 to 2 M.

11. A process according to claim 10, wherein the concentration is from M/4 to M.

12. A process according to claim 3, wherein the extraction is carried out at a temperature from 20° to 280° C.

13. A process according to claim 12, wherein the temperature is from 80° to 220° C.

14. A process according to claim 3, wherein the extraction period is from 0.5 to 192 hours.

15. A process according to claim 14, wherein the extraction period is from 1 to 120 hours.

16. A process according to claim 5, wherein upon extraction the liquid/solid weight ratio is from 2:1 to 25:1.

17. A process according to claim 16, wherein the ratio is from 5:1 to 20:1.

18. A process according to claim 5, wherein upon extraction the concentration of the complexing agent, in moles per liter, is from M/10 to 2 M.

19. A process according to claim 18, wherein the concentration is from M/5 to M.

20. A process according to claim 5, wherein the complexing agent is a salt of ethylenediamine tetraacetic acid, and a base is used together with the complexing agent in a concentration, in moles per liter, from M/10 to 2 M.

21. A process according to claim 20, wherein the concentration is from M/5 to 1.5 M.

22. A process according to claim 5, wherein the complexing agent is a salt of ethylenediamine tetraacetic acid, and the extraction is carried out at a temperature from 40° to 180° C.

23. A process according to claim 22, wherein the temperature is from 60° to 150° C.

24. A process according to claim 5, wherein the complexing agent is a salt of ethylenediamine tetraacetic acid, and the extraction period is from 6 to 192 hours.

25. A process according to claim 24, wherein the extraction period is from 12 to 96 hours.

26. A process according to claim 5, wherein the complexing agent is a salt of diethylenetriamine pentaacetic acid, and a base is used together with the complexing agent in a concentration, in moles per liter, from M/2 to 2 M.

27. A process according to claim 26, wherein the concentration is from M to 1.5 M.

28. A process according to claim 5, wherein the complexing agent is a salt of diethylenetriamine pentaacetic acid, and the extraction is carried out at a temperature from 20° to 125° C.

29. A process according to claim 28, wherein the temperature is from 40° to 110° C.

30. A process according to claim 5, wherein the complexing agent is a salt of diethylenetriamine pentaacetic acid, and the extraction period is from 6 to 144 hours.

31. A process according to claim 30, wherein the period is from 12 to 72 hours.

32. A process according to claim 3, wherein upon extraction the liquid/solid weight ratio is from 2:1 to 25:1; the concentration of the precipitating agent, in moles per liter, is from M/10 to 2 M; a base is used together with the extraction agent, and the concentration of said base, in moles per liter, is from M/10 to 2 M; the extraction is carried out at a temperature from 20° to 280° C.; and the extraction period is from 0.5 to 192 hours.

33. A process according to claim 32, wherein the liquid/solid weight ratio is from 5:1 to 20:1; the precipitating agent concentration is from M/5 to 1.5 M; the base concentration is from M/4 to M; the extraction temperature is from 80° to 220° C.; and the extraction period is from 1 to 120 hours.

34. A process according to claim 5, wherein upon extraction the liquid/solid weight ratio is from 2:1 to 25:1; upon extraction the concentration of the complexing agent, in moles per liter, is from M/10 to 2 M; the complexing agent is a salt of ethylenediamine tetraacetic acid; a base is used together with the complexing agent in a concentration, in moles per liter, from M/10 to 2 M; the extraction is carried out at a temperature from 40° to 180° C.; and the extraction period is from 6 to 192 hours.

35. A process according to claim 34, wherein the liquid/solid weight ratio is from 5:1 to 20:1; the complexing agent concentration is from M/5 to 1.5M; the base concentration is from M/5 to 1.5 M; the extraction temperature is from 60° to 150° C.; and the extraction period is from 12 to 26 hours.

36. A process according to claim 5, wherein upon extraction the liquid/solid weight ratio is from 2:1 to 25:1; upon extraction the concentration of the complexing agent, in moles per liter, is from M/10 to 2 M; the complexing agent is a salt of diethylenetriamine pentaacetic acid, a base is used together with the complexing agent in a concentration, in moles per liter, from M/2 to 2 M; and the extraction is carried out at a temperature from 20° to 125° C.; and the extraction period is from 6 to 144 hours.

37. A process according to claim 36, wherein the liquid/solid weight ratio is from 5:1 to 20:1; the complexing agent concentration is from M/5 to M; the base concentration is from M/5 to 1.5 M; the extraction concentration is from M to 1.5 M; the extraction temperature is from 40° to 110° C.; and the period is from 12 to 72 hours.

38. A process according to one of claim 2, wherein the starting zeolite and the zeolite ZK 5 obtained are both in agglomerated form.

* * * * *